United States Patent [19]
Barnett et al.

[11] Patent Number: 5,322,684
[45] Date of Patent: * Jun. 21, 1994

[54] COSMETIC DELIVERY SYSTEM

[75] Inventors: Philip J. Barnett, Parkgate; Michael R. Lowry, Chester, both of United Kingdom

[73] Assignee: Elizabeth Arden Co., Division of Conopco, Inc., New York, N.Y.

[ * ] Notice: The portion of the term of this patent subsequent to Dec. 7, 2010 has been disclaimed.

[21] Appl. No.: 911,548

[22] Filed: Jul. 9, 1992

[30] Foreign Application Priority Data

Jul. 15, 1991 [GB] United Kingdom ............... 9115278

[51] Int. Cl.$^5$ .............................................. A61K 9/12
[52] U.S. Cl. ........................................ 424/47; 424/46; 424/401; 239/3
[58] Field of Search ......................... 424/46, 47, 401

[56] References Cited

U.S. PATENT DOCUMENTS 4,776,515 10/1988 Michalchik ..................... 239/3

FOREIGN PATENT DOCUMENTS

| | | |
|---|---|---|
| 0029301 | 5/1981 | European Pat. Off. . |
| 0031649 | 7/1981 | European Pat. Off. . |
| 0132062 | 1/1985 | European Pat. Off. . |
| 0163390 | 12/1985 | European Pat. Off. . |
| 0171184 | 2/1986 | European Pat. Off. . |
| 0224352 | 6/1987 | European Pat. Off. . |
| 0234842 | 9/1987 | European Pat. Off. . |
| 0253539 | 1/1988 | European Pat. Off. . |
| 0243031 | 7/1989 | European Pat. Off. . |
| 0368494 | 5/1990 | European Pat. Off. . |
| 0441501 | 8/1991 | European Pat. Off. . |
| 0468735 | 1/1992 | European Pat. Off. . |
| 0468736 | 1/1992 | European Pat. Off. . |
| 5697214 | of 0000 | Japan . |
| 8500761 | 2/1985 | PCT Int'l Appl. . |
| WO90/00446 | 1/1990 | PCT Int'l Appl. . |
| WO90/03224 | 4/1990 | PCT Int'l Appl. . |
| 1393333 | 5/1975 | United Kingdom . |
| 1569707 | 6/1980 | United Kingdom . |
| 2061769 | 5/1981 | United Kingdom . |
| 2073052 | 10/1981 | United Kingdom . |
| 2092025 | 8/1982 | United Kingdom . |

Primary Examiner—Thurman K. Page
Assistant Examiner—Jyothsna Venkat
Attorney, Agent, or Firm—Milton L. Honig

[57] ABSTRACT

A potent cosmetically active material such as a perfume is delivered to the body by electrostatic spraying. The active material can be sprayed at ultra-low flow rates, preferably in neat or substantially neat form.

6

COSMETIC DELIVERY SYSTEM

FIELD OF THE INVENTION

This application relates to a system for delivering cosmetically active materials to the body. More particularly the invention relates to methods and apparatus for applying such materials to the body using the principle of electrostatic spraying. The invention is particularly useful for delivering potent cosmetically active materials which require delivery in very small quantities.

BACKGROUND OF THE INVENTION

Conventional systems for applying potent cosmetically active materials, such as perfumes, to the body, especially onto the skin, rely on solvent dilution to deliver sufficiently low concentrations of these actives. The presence of the solvent, however, may limit the effectiveness of the active material, for example by physical and/or chemical interactions, particularly on storage, and also restricts the range of cosmetic actives which can be delivered by these known systems.

Hitherto, perfumes for example are generally delivered from pressurized containers and in the form of a solution of the perfume active in a suitable solvent such as an alcohol. Such delivery systems are inefficient, bulky, heavy and expensive. A further problem associated with these known systems, as well as being noisy to use and having poor sensory appeal, i.e. generating cold, wet sprays, is that there is significant waste through loss of the active material to the atmosphere which also results in unwanted atmospheric mists and contamination to the user's eyes and other body parts, which may present respiratory or other health problems to the user. This is particularly problematic in shops and department stores for example, where many perfume sprays are frequently tested by potential customers, giving rise to considerable atmospheric pollution and waste. The use of aerosol propellants which are volatile organic compounds are also now well recognised as being environmentally unfriendly, possibly hazardous to health and indeed are being legislated against in many countries of the world.

In a very different technical field, the principle of electrostatic spraying of liquid and solid materials is also known. In this technique a formulation to be sprayed is raised to a high electric potential in a spray nozzle to cause the formulation to atomise as a spray of electrically charged droplets. Such electrically charged droplets seek the closest earthed object to discharge their electric charge, and this can be arranged to be the desired spray target. Hitherto, electrostatic spraying techniques have been proposed principally for only large-scale industrial and agricultural applications, especially for delivering reactive materials like paints, adhesives and other surface coatings, as well as large-scale delivery of pesticides and other agricultural or agrochemical formulations. Examples of disclosures in this field include GB-A-1393333, GB-A-1569707, GB-A-2092025, EP-A-029301, EP-A-253539 and WO-A-85/00761, the contents of which disclosures are incorporated herein by reference.

More recently, there have been a small number of proposals for utilising the known principle of electrostatic spraying for delivering particular materials in specific applications other than those mentioned above.

EP-A-224352 suggests the use of an electrostatic sprayer for delivering a pharmaceutically active agent to the eye, to replace conventional ocular treatment using eye drops.

JP-A-56-97214 (dating from 1981) suggests the use of electrostatic spraying for applying a granular (i.e. solid particles of) colouring material to hair to effect surface coating thereof.

Also to be mentioned, though of less relevance, is U.S. Pat. No. 4,776,515, which proposes an electrodynamic fine particle negative ion generator adapted to spray various liquids, particularly water, but possibly also alcohol, perfume, ammonia, liquid medications and surfactants. The object of the disclosed system is to provide an ozone-free mist of negatively ionised liquid particles, (which presupposes that the material to be sprayed is ionizable), and the mist that is produced instantly disperses into an open area in which the apparatus is operated, e.g. a room, so that a far-reaching, uniform aerosol is generated which has particular applicability for large public areas such as hospitals, restaurants and offices. Clearly, this system is unsuitable for small-scale personal use and in many of its objects goes directly against the principles upon which a solution to the above mentioned prior art problems must be founded.

SUMMARY OF THE INVENTION

As a result of identifying and appreciating the above problems, prejudices and limitations of the known art and through much experimentation, we have now devised a system which enables the principle of electrostatic spraying to be put to effective use in delivering potent cosmetically active materials, such as perfumes and the like, to the body, such that apparatus and methods are now provided for such delivery regimes which are technically efficient, cost effective, safe, have widespread consumer applicability and appeal, and which solve or at least ameliorate many, if not all, of the problems associated with the prior art.

Accordingly, in a first aspect the present invention provides a method of delivering a potent cosmetically active material to the body, comprising electrostatically spraying the material thereon.

In more detail, the method of this aspect of the invention preferably comprises:

(a) providing an apparatus which includes:

(i) a reservoir containing the potent cosmetically active material to be delivered which is in an electrostatically sprayable form;

(ii) at least one delivery means in communication with the reservoir;

(iii) a high voltage generator powered from an electricity source;

(iv) control means for selectively applying the high voltage from the generator to the or each delivery means;

(b) actuating the said control means to electrostatically spray the potent cosmetically active material from the or each delivery means onto the body at an intended site.

In a second aspect, the present invention provides apparatus for delivering a potent cosmetically active material to the body, comprising:

(a) a reservoir for containing the potent cosmetically active material which is in an electrostatically sprayable form;

(b) at least one delivery means in communication with the reservoir;

(c) a high voltage generator powered from an electricity source;
(d) control means for selectively applying the high voltage from the generator to the or each delivery means to electrostatically spray the potent cosmetically active material from the or each delivery means.

In a third aspect, the present invention provides, in combination, the apparatus as defined above and an electrostatically sprayable composition consisting of or consisting essentially of or containing one or more potent cosmetically active materials.

In the above defined aspects of the invention, particularly preferred cosmetically active materials to which the invention may be applied are in neat or substantially neat form.

Having thus defined the main aspects of the present invention, preferred embodiments and various optional features and characteristics thereof will now be described, with reference to the accompanying drawing.

Figure 1:
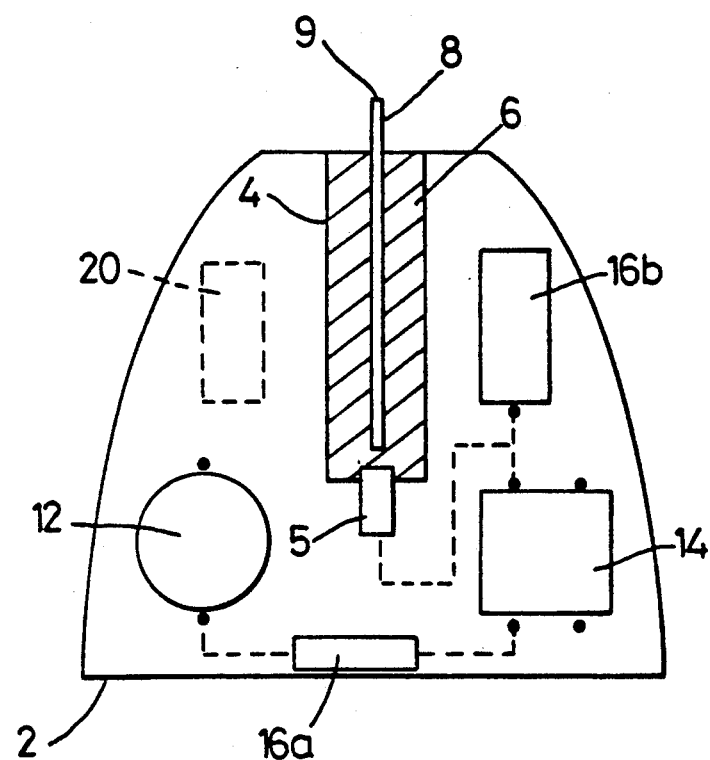
FIG. 1 is a schematic median view of one preferred embodiment of the apparatus according to the present invention.

DESCRIPTION OF PREFERRED EMBODIMENTS

A principal advantage of the delivery system according to the present invention is that it allows the potent cosmetically active material to be delivered to the body in neat or substantially neat form; that is to say, it comprises only the potent cosmetically active material itself or contains only small amounts of one or more adjunct materials such as for example solvents or materials necessary for adjusting the electrostatic spraying parameters of the composition. If the potent cosmetically active material is not neat, then it preferably contains less than 10% by weight, more preferably less than 5% by weight, even more preferably less than 1% by weight, of such adjunct materials.

As a result of the preferred highly concentrated nature of the potent cosmetically active material which may be sprayed in accordance with the invention, the composition to be delivered may be done so at ultra-low flow rates, for example at flow rates of a corresponding order of magnitude lower than the order of magnitude of dilution using solvent(s) of conventional compositions, e.g. perfume sprays, found in the prior art. Suitable and preferred flow rates in the context of this invention are discussed further below.

Particularly preferred potent cosmetic actives for use in the present invention are perfume materials, e.g. perfume oils. The invention may however be applied to any other cosmetic active which is similarly potent and conventionally delivered in very small quantities. Examples of such other potent cosmetic actives for use in the invention include: spot treatment materials, e.g. ethyl lactate, benzoyl peroxide; skin blemish treatment agents, e.g. for treating freckles; wart removers; skin conditioning agents, e.g. perfluoropolyether materials; and mixtures thereof.

Examples of perfume materials such as essential oils and aroma chemicals which may be delivered using the present invention include the following: Ambergris, Clove, Jasmine, Labdanum, Melilot, Musk, Myrrh, Olibanum, Sandalwood, Benzyl acetate, Benzyl salicylate, Citronellol, Coumarin, Geraniol, Linalool, Linalyl acetate, Musk ambrette, Terpinyl acetate.

Potent cosmetically active materials such as any of the above may be delivered in accordance with the invention either singly or in combination.

If necessary or if desired, the potent cosmetically active material or materials to be delivered may be provided in the form of compositions including an amount of one or more solvents or diluents which solubilise, are soluble in, or are miscible with the active material. Preferably such solvents or diluents are present in minor amounts. Such solvents or diluents may be any of those currently known for that purpose, for example alcohols and certain esters. Examples of suitable solvents or diluents include ethanol, isopropyl alcohol, propylene glycol, dipropylene glycol, phenylethyl alcohol, glycerol, 1,3-butanediol, 1,2-propanediol, isoprene glycol, diethyl phthalate.-

Generally there is the essential overall requirement of potent cosmetically active material(s) or compositions containing them which are useful in the present invention that they be electrostatically sprayable.

A principal characteristic of such electrostatically sprayable material(s) or compositions which it will usually be necessary to carefully select or adjust as necessary (as discussed further below), is their resistivity. Preferred resistivities fall within the range from about $10^4$ to about $10^{12}$ ohm cm, more preferably from about $10^6$ to about $10^{10}$ ohm cm. Resistivities of lower than $10^4$ may possibly be used. Resistivities of more than about $10^{12}$, e.g. up to about $10^{14}$ or more, may also be used, though such values are difficult to measure using cheap, conventional resistance measuring apparatus. Resistivity is measured using standard, conventional apparatus and methods, generally at 25° C.

In accordance with the invention, therefore, the potent cosmetically active material or composition containing same may optionally include a suitable amount of one or more resistivity adjusting materials. A suitable amount for a given system may depend upon the type or types of active material used and possibly other spraying parameters and is readily determinable by simple experiment. Suitably, polar substances such as alcohols, e.g. ethanol, may be used to lower the resistivity of a given cosmetic active, whereas non-polar substances, e.g. oils and other hydrophobic materials, may be used to increase its resistivity. Alternative resistivity adjusting materials include charged species such as salts, e.g. sodium chloride, or a salt conventionally used in buffers in personal products or pharmacological formulations.

In addition to resistivity, another parameter of the materials or compositions to be sprayed which it may be necessary to carefully select or adjust is viscosity.

Potent cosmetically active materials and compositions containing same of a wide range of viscosities may be suitable for use in the present invention, but suitably the viscosity is in the range of from about 0.1 to about 50000 mPas, more preferably from about 0.1 to about 10000 mPas, even more preferably from about 0.5 to about 5000 mPas (at 25° C). If desired or as necessary one or more viscosity adjusting agents may be included. Examples of such agents include salts, e.g. alkali metal or ammonium halides, polymers and conventional thickening materials, and oils and polar oil thickeners such as cosmetic oils, waxes, glycerides and suitable amphiphiles with melting points of for example $>20°$ C.

Viscosity may in fact be used as a parameter to control the rate of delivery of the cosmetic active to the intended site, as it has been found to have a substantially inverse proportionality relationship with the flow rate of the material or composition from the delivery means. For example, the identity of the potent cosmetic active or a habit or need of a user may dictate an optimum delivery rate, in which case careful selection of the viscosity of the material or composition to be sprayed can provide a self-regulating deposition mechanism.

For use in the present invention, the hardware and electrical componentry and circuitry may be of any suitable construction and design. The art of electrostatic spraying contains many examples of suitable apparatus which may be used in the present invention and such disclosures of such apparatus or particular features thereof may be applied either singly or in combination to the spray systems of the present invention.

Examples of suitable electrostatic spraying hardware include, in addition to those of the prior art references mentioned above, those of the following published references: GB-A-2061769, GB-A-2073052, EP-A-031649, EP-A-132062, EP-A-163390, EP-A-171184, EP-A-234482, EP-A-243031, EP-A-368494, EP-A-441501, EP-A-468735 and EP-A-468736; the disclosures of all of which are incorporated herein by reference.

As will be appreciated by persons skilled in the art, particular constructional features and design and electrical and other operating parameters of such apparatuses may be selected or adjusted as necessary, in the context of the present invention, in accordance with the desired functioning characteristics, as for example dictated by the composition or material to be sprayed and/or the needs or wishes of a user.

Features of the apparatus of the present invention which may be so selected and/or adjusted include for example: voltage generated by the high voltage generator and power source, electric field strength in or in the region of the product delivery means, flow rate of the product to be sprayed from the reservoir to and out of the delivery means, size and configuration of the delivery means itself and construction and properties of any product feed mechanism utilised between the reservoir and the output of the delivery means.

In preferred embodiments of the invention, preferred voltages generated by the high voltage generator from the power source are in the range of from about 2 to about 12 kilovolts, more preferably from about 5 to about 10 kilovolts, even more preferably from about 6 to about 8 kilovolts. The most suitable voltage for a given system may depend upon the product to be sprayed, as well as other parameters, all of which will generally be selected to give an overall optimised system.

Electric field strengths which are responsible for the spraying action of the electrostatic apparatus will be largely dependent upon the voltage applied. However, field strengths may be controlled or adjusted if necessary, for example by changes in nozzle configuration or geometry and/or the use of field intensifying electrodes, which are well known in the art cited above.

Optimum flow rates of product to be sprayed will often depend upon the composition of the product itself, especially upon the concentration of the active ingredient being applied. Also, as already mentioned with respect to viscosity of the sprayable material, a suitable flow rate may be selected depending upon the identity of the potent cosmetic active and/or habit or needs of a user. By way of example, preferred flow rates of compositions for delivery in accordance with embodiments of the invention are in the range of from about 0.00001 to about 0.01 ml/sec, more preferably from about 0.0001 to about 0.001 ml/sec. These flow rates will generally be for a single product delivery means. In embodiments of the apparatus of the invention which employ a plurality of such delivery means, it may be more appropriate to base the selected flow rate on the overall total flow rate of all the delivery means, in which case the optimum flow rate per delivery means may be correspondingly lower than the above preferred values.

The size and configuration of the one or more delivery means in the apparatus of the invention may be of any suitable form and again may be selected in association with other parameters to give an optimised functioning electrostatic spray delivery system. Commonly the or each delivery means will be in the form of a nozzle, preferably of insulating or semi-insulating material such as plastics or various polymers, as is well known in the art.

As a result of certain of the advantages associated with the present invention, namely the provision of a spray which is silent, invisible and of a ultra-low flow rate, and because the cosmetically active material to which the invention is particularly directed is a potent active such as a perfume, it is a particularly preferred feature of methods and apparatuses in accordance with the invention that there are provided means for providing dosage control so that overdosage of the potent cosmetic active is avoided. Such dosage control means preferably comprise means for actuating the spraying apparatus for a predetermined period of time. Alternatively or additionally the dosage control means may comprise means for delivering a predetermined amount of product from the or each delivery means, such as to provide a fixed dosage mechanism with or without control of the spray delivery time. For the above purposes, suitable control circuitry comprising an electronic timer and switch may be included in the apparatus, as may any suitable known metering means which supply a predetermined fixed amount of product from the reservoir to the or each delivery means.

In preferred embodiments of the apparatus of the invention, the or each delivery means is in communication, i.e. preferably fluid communication, with the reservoir or reservoirs (if for example more than one material or composition is to be desired to be sprayed from the same apparatus or even the same delivery means) by virtue of product feed means. As is well described in the prior art, such feed means may comprise a wick, e.g. a porous wick, through and/or over which the product to be sprayed flows before reaching the point of high electric field strength where it is dispersed as a charged spray of droplets or particles. Alternatively the feed means may comprise a hollow conduit through which the composition passes under the effect of capillary action.

As is well known in the art, the apparatus according to the invention preferably include a trigger (i.e. a manual control means) or alternatively an automatic control means to selectively apply the high voltage from the generator to the or each delivery means to electrostatically spray the neat or substantially neat cosmetic active onto the desired site on the body. Any other suitable control means however, e.g. which automatically control actuation of the system, may be used, as will be appreciated by persons skilled in the art.

There now follows a description of one preferred embodiment of the apparatus of the present invention, in conjunction with which reference should be had to the accompanying FIG. 1.

As shown schematically in the Figure, the electrostatic spraying apparatus comprises a housing 2 of insulating material, e.g. a plastics moulding, which contains the various hardware components of the system to provide a lightweight, hand-held unit that is convenient and easy to manipulate and use.

Within the housing 2 are provided the various components of the electrostatic spraying system, comprising the following main elements: power source 12, high voltage generator 14, additional circuitry 16a and 16b, operation control means 20, reservoir 4, product 6 to be sprayed and delivery means 8 from the end portion 9 of which the product 6 is sprayed. Each of these elements will now be described in more detail.

The power source 12 is conveniently a low voltage battery such as a conventional 1.5 volt cell as used in small electrical devices such as electronic calculators and watches. The high voltage generator 14 is a transformer which converts a low AC voltage produced by the additional circuitry 16a into a high AC voltage which is then fed to the electrostatic spraying head elements via additional circuitry 16b. The latter additional circuitry includes for example one or more capacitors and diodes for, among other things, converting the high AC voltage from the transformer 14 to a high DC voltage.

Included as the elements of the electrostatic spraying head are the reservoir 4 containing the product 6 to be sprayed and the product delivery means 8. Electrical contact means 5 are provided to enable the product 6 to be raised to the high electric potential generated by the high DC voltage produced by the electrics of the apparatus. The product 6 is, in a preferred embodiment, a neat or substantially neat perfume oil, such as those already known for delivery in a solution in an alcohol solvent in conventional perfume sprays. Depending upon the identity of the perfume oil, one or more resistivity and/or viscosity adjusting agents may be included in the product 6 to be sprayed, as has already been described.

The delivery means 8 in the illustrated embodiment is a wick of porous material, e.g. a porous polymeric material, through which the product 6 is drawn to its tip 9 by capillary action. At the tip 9 the high electric field strength causes the product to be ejected from the tip, for example at first in the form of a thin ligament, but in any event ultimately as an atomised spray of electrically charged droplets which seek the closest earthed object to discharge their electric charge. In use, the earthed target is a part of the body, e.g. the skin, onto which it is desired to deliver the potent cosmetically active material.

In an alternative preferred embodiment of the apparatus, the tip 9 of the delivery means 8 may be in the form of a nozzle having a crown-like configuration, with the delivery means 8 preferably providing a narrow conduit through which the product 6 is drawn to the nozzle under capillary action, as disclosed in EP-A-0243031, the disclosure of which is incorporated herein by reference. In this arrangement the electric field strength at the plurality of projecting portions of the nozzle is sufficiently large compared with the remaining edge areas of the nozzle to cause the product 6 to be electrostatically projected from the tip of the delivery element 8 at each of those plurality of locations on the nozzle.

The apparatus illustrated schematically in FIG. 1 further includes a microswitch 20 which constitutes the control means for actuating the apparatus by applying, when the switch is operated, the high voltage from the electrics to the delivery means. The location of the microswitch 20 in the apparatus is preferably chosen so as to be readily operatable by the user, e.g. using a finger, when the apparatus is held in the hand and directed towards the desired area of the body, ready for use.

We claim:

1. A method for a user to deliver a potent cosmetically active material as a cosmetic to the user's body, comprising the user electrostatically spraying from a hand held apparatus said material onto the user's body, the cosmetically active material being a perfume, and the method further comprising:
   (a) providing an apparatus which includes:
      (i) a reservoir containing the potent cosmetically active material to be delivered which is in an electrostatically sprayable form;
      (ii) at least one delivery means which is a nozzle in communication with the reservoir;
      (iii) a high voltage generator generating voltage in the range 2 to 12 kilovolts powered from an electricity source;
      (iv) control means for selectively applying the high voltage from the generator to the at least one delivery means; and
   (b) actuating the said control means to electrostatically spray the potent cosmetically active material from the at least one delivery means onto the body at an intended site.

2. A method according to claim 1, wherein the potent cosmetically active material is in neat form.

3. A method according to claim 1, wherein the potent cosmetically active material is in the form of a composition comprising less than 5% by weight of material other than the said potent cosmetically active material.

4. A method according to claim 3, wherein the composition comprises less than 1% by weight of material other than the said potent cosmetically active material.

5. A method according to claim 2, wherein the potent cosmetically active material is delivered at a rate of from 0.00001 to 0.01 ml/sec.

6. A method according to claim 1, further comprising providing dosage control means for limiting the amount of potent cosmetically active material which is delivered.

* * * * *